(12) United States Patent
Wortelboer et al.

(10) Patent No.: US 11,224,334 B2
(45) Date of Patent: Jan. 18, 2022

(54) RADIAL ILLUMINATION SYSTEM WITH FERRULE

(71) Applicant: KONINKLIJKE PHILIPS N.V., Eindhoven (NL)

(72) Inventors: Pippinus Maarten Robertus Wortelboer, Eindhoven (NL); Antonius Johannes Josephus Rademakers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 734 days.

(21) Appl. No.: 15/748,891

(22) PCT Filed: Aug. 4, 2016

(86) PCT No.: PCT/EP2016/068632
§ 371 (c)(1),
(2) Date: Jan. 30, 2018

(87) PCT Pub. No.: WO2017/025423
PCT Pub. Date: Feb. 16, 2017

(65) Prior Publication Data
US 2019/0008376 A1     Jan. 10, 2019

(30) Foreign Application Priority Data
Aug. 13, 2015  (EP) .................................... 15180989

(51) Int. Cl.
| A61B 1/06 | (2006.01) |
| A61B 1/00 | (2006.01) |
| A61B 1/07 | (2006.01) |
| A61B 5/00 | (2006.01) |
| A61B 18/24 | (2006.01) |
| A61B 18/22 | (2006.01) |
| A61B 18/00 | (2006.01) |

(52) U.S. Cl.
CPC ........ A61B 1/0607 (2013.01); A61B 1/00177 (2013.01); A61B 1/07 (2013.01);
(Continued)

(58) Field of Classification Search
CPC ..... A61B 1/0607; A61B 1/00177; A61B 1/07; A61B 5/0084; A61B 5/6852; A61B 18/24;
(Continued)

(56) References Cited

U.S. PATENT DOCUMENTS

| 4,994,060 A | 2/1991 | Rink et al. |
| 5,130,536 A | 7/1992 | Sato et al. |

(Continued)

FOREIGN PATENT DOCUMENTS

| CN | 2615690 Y | 5/2004 |
| JP | H0695027 A | 4/1994 |

(Continued)

OTHER PUBLICATIONS

Hoffstein, V. et al. (1991). "The acoustic reflection technique for non-invasive assessment of upper airway area", The European respiratory journal, 4(5), 602-11.

*Primary Examiner* — Timothy J Neal
*Assistant Examiner* — William B Chou

(57) ABSTRACT

A radial illumination system is for projecting a light pattern radially. A light source generates a light output to an optical fiber. A ferrule is provided around the end of the optical fiber, and a reflector is mounted over or in the ferrule or integral with the ferrule, for redirecting the light to form generally radial light. In this way, a simple design with low component count is able to perform the optical alignment and optical reflecting functions.

14 Claims, 4 Drawing Sheets

(52) U.S. Cl.
CPC .......... *A61B 5/0084* (2013.01); *A61B 5/6852* (2013.01); *A61B 18/24* (2013.01); *A61B 2018/00345* (2013.01); *A61B 2018/00494* (2013.01); *A61B 2018/00541* (2013.01); *A61B 2018/00982* (2013.01); *A61B 2018/2272* (2013.01)

(58) Field of Classification Search
CPC .......... A61B 2018/00345; A61B 2018/00494; A61B 2018/00541; A61B 2018/00982; A61B 2018/2272
See application file for complete search history.

(56) References Cited

U.S. PATENT DOCUMENTS

| | | |
|---|---|---|
| 2004/0078032 A1 | 4/2004 | Frenz et al. |
| 2007/0232874 A1* | 10/2007 | Ince .................... A61B 5/0261 600/320 |
| 2008/0077198 A1* | 3/2008 | Webb .................... A61N 5/0618 607/88 |
| 2010/0060821 A1 | 3/2010 | Wang et al. |
| 2011/0170278 A1 | 7/2011 | Tordini |
| 2011/0317959 A1 | 12/2011 | Ohta et al. |
| 2012/0155110 A1 | 6/2012 | Pijlman et al. |
| 2015/0209106 A1* | 7/2015 | Sliwa .................... A61B 5/0036 600/477 |
| 2017/0105608 A1* | 4/2017 | Kura .................. G02B 23/2423 |
| 2017/0127925 A1* | 5/2017 | Honda .................... G02B 23/26 |

FOREIGN PATENT DOCUMENTS

| | | |
|---|---|---|
| JP | 2004325522 A | 11/2004 |
| JP | 2006235346 A | 9/2006 |
| WO | 2010006082 A1 | 1/2010 |

* cited by examiner

RADIAL ILLUMINATION SYSTEM WITH FERRULE

CROSS-REFERENCE TO PRIOR APPLICATIONS

This application is the U.S. National Phase application under 35 U.S.C. § 371 of International Application Serial No. PCT/EP2016/068632, filed on 4 Aug. 2016, which claims the benefit of European Application Serial No. 15180989.4, filed on 13 Aug. 3015. These applications are hereby incorporated by reference herein.

FIELD OF THE INVENTION

The invention relates to a radial illumination system, for example for use in a radial imaging system.

BACKGROUND OF THE INVENTION

An example of a radial imaging system is a system for collecting images of the interior wall of a passageway.

One use of such an arrangement is part of a catheter camera, in which the cross section of a passageway in which the catheter is located is to be inspected.

A catheter camera for example comprises a radial imaging system. A radial illumination system generates an annular line of illumination which is projected onto the interior wall. A reflecting cone redirects light which, after reflection (and scattering) at the interior wall, is received (mainly) radially inwardly. The light is redirected towards an essentially axial direction, for collection by an axially aligned camera. The cross section of a passageway in which the catheter is located is to be imaged by the camera.

An example of the use of such a catheter camera is for analysis of the upper airway, for determining the causes of obstructive sleep apnea.

Obstructive sleep apnea (OSA) is the most common kind of sleep apnea, affecting up to one in eighteen people, and is characterized by the occurrence of pauses in breathing, or instances of shallow or infrequent breathing, during sleep. It is caused by blockage or obstruction of the oral cavity or upper airway, often due to loss of muscular tone induced by the onset of old age, or (temporary) by abuse of drugs or alcohol.

A range of therapies exist for treatment of OSA, the most common of which is positive airway pressure (PAP), in which a ventilator is used to deliver a stream of air through the airway at a controlled pressure, in order to hold open the airway. PAP is needed in more severe cases, where patients exhibit an apnea hypopnea index (AHI)>30. OSA patients may also suffer from daytime sleepiness and require therapy to prevent the development of comorbidities over the longer term. Mild-moderate OSA patients often have more difficulty adhering to PAP therapy because the disease burden is not as strong as in severe patients, and are therefore reluctant to submit to so invasive a therapy. In these cases, various alternative treatments exist, such as positional therapy, mandibular advancement (oral appliances), upper airway surgery and implantable devices.

In each of these therapies, however, it is important to understand which part(s) of the upper airway in particular is (are) causing obstruction, such that the therapy can be directed most effectively. This explains the interest in dynamic examinations of the upper airway preferably in a non-invasive way. One approach is to perform an examination of the airway non-invasively using acoustic reflectometry techniques. In such techniques, acoustic waves are propagated along the airway of the patient, by an emitter, via the mouth or nose, and reflections are listened for using a microphone adjacent to the emitter. It is possible, through algorithmic analysis of the detected reflections (see for example: Hoffstein, V., and J. J. Fredberg. "The acoustic reflection technique for non-invasive assessment of upper airway area." European Respiratory Journal 4.5 (1991): 602-611.), to determine an estimate of the cross-sectional area of the examined airway as a function of distance from the emitter. From this, narrowing of the airway at particular locations can be identified, and the specific positions therefore of airway obstructions ascertained.

Reflectometry techniques however suffer the disadvantage that the accuracy of cross-sectional area estimations is limited and certainly declines with distance from the emitter. This is amongst others compounded by acoustic leakage and also patient movements during the measurement process, which both act to further compromise the accuracy of the obtained results. Furthermore, since the first obstruction encountered by a wave propagating along the airway causes reflection of much of the wave's initial intensity, reflections from subsequent portions of the airway are typically too weak in intensity to derive any accurate measurements. Hence it is typically only possible to accurately determine the location of the upper-most airway obstruction using these techniques. The technique cannot provide shape information of the cross section.

It is known instead to use endoscopic procedures, in particular procedures for inspecting or investigating the patency of the human upper airway. Using a standard flexible endoscope for airway examination, specific sites in the upper airway can be inspected for some time to see whether temporary obstructions occur. This however requires the endoscope to be moved from one spot to the other during an examination which is time-consuming and inconvenient for the patient. For this reason endoscopic examination during natural sleep did not become part of common practice. An alternative version which has acquired some acceptation in current practice involves bringing the patient to artificial sleep by means of sedative drugs. This is believed to cause collapses at sites that also participate in real sleep apneas and hypopneas. Also the sedation relieves the discomfort of endoscope travel.

To inspect the upper airway at some discrete critical sites, it is also possible to use a catheter with multiple image sensors; once the catheter has been inserted it can remain in the same position during a longer period without additional discomfort for the patient.

Image sensors can be used to obtain a measure of radial distance, for example if the image sensor is combined with an illumination element that projects a structured illumination pattern (e.g. a ring) on the inside of the airway, the captured image sensor information in respect of the ring image can be analyzed to derive distance information (e.g. by triangulation), and thereby enable the shape of the internal airway passage to be derived.

For example, an endoscope may have one or more light generating means capable of producing an outwardly directed ring (or radial plane) of light, such that when inserted into a tube-like airway, cross sectional contours of the airway may be illuminated for inspection by a camera.

One known means of providing such a light pattern is to direct collimated laser light from an optical fiber toward a deflecting cone whose angle is such as to deflect the incident light radially, for example at 90 degrees, from its surface in all directions around it. The effect is to create a 'ring' pattern of light projecting outwards from the cone, which may then be used to illuminate a circumferential section of an airway. In particular, there are two variations of this concept. In a first, the cone has a reflective outer surface, and is arranged with its tip facing in the direction of the oncoming light, such that light is reflected directly out from its surface. In a second, the cone is arranged with its base facing toward the oncoming light and the cone tip angle selected such that light incident from the optical fiber on the internal walls of the cone is reflected by total internal reflection in the direction of the opposing wall, through which it is transmitted, deflecting due to refraction as it does so into a path which is at 90 degrees to the initial incident light.

The reflected light is then captured by a camera. This may be achieved by positioning the camera with the inner wall being examined within the field of view, or else another reflecting cone may be used to redirect the reflected light back to an almost axial direction for capture by an axially aligned camera.

It is possible to create multiple ring patterns of light, at a series of spaced points along the airway. This can for example be achieved by means of providing multiple illumination units along the catheter, each with its own laser, optical fiber (optionally a GRIN lens) and cone.

One issue with known designs of this type is that the illumination unit contains many different components that need to be carefully aligned during assembly. Therefore it is extremely difficult to miniaturize the unit and to reduce manufacturing cost. The known approach makes use of a laser fiber, a collimating element, a deflecting element and a transparent housing. In principle the collimation and deflection function can be integrated into a single piece with a well-designed (concave) reflective cone surface. However, the alignment of the laser fiber and this cone is extremely critical and requires a transparent housing of excellent optical quality. It is also possible to use a non-transparent housing for alignment and assembly in combination with a total internal reflection element. This only works for a collimated laser beam, so still requires a separate collimator.

There is therefore a need for a design which simplifies the optical components between the light source and the radial light pattern that is to be projected.

SUMMARY OF THE INVENTION

The invention is defined by the claims.

According to an aspect of the invention, there is provided a radial illumination system for projecting a light pattern radially comprising:

a light source for generating a light output;

an optical fiber which is adapted to transmit the light output and to emit the light in a direction centered along an axis, from an end of the optical fiber;

a ferrule around the end of the optical fiber; and a reflector coupled to or integral with the ferrule, for redirecting the emitted light to form a ring of generally radial light around the axis, wherein the ferrule comprises a reflecting face which faces away from the end of the optical fiber, and the reflector comprises a cap which is mounted over end of the ferrule and which has a reflecting surface which faces the end of the optical fiber, such that an optical path is defined from the end of the optical fiber, to the reflecting surface and then to the reflecting face.

In this system, a ferrule is used to fix the position of the reflector relative to the optical fiber as well as terminating the optical fiber. This provides a reduction in the number of components needed to provide accurate optical alignment within the system.

The arrangement provides a double reflection path from the optical fiber to form the radial light. The optical fiber light output reflects from the reflecting surface of the cap back to the reflecting face of the ferrule, and the light is then reflected to its final radial direction. This provides a compact design, which can be kept small by keeping the distance between the end of the optical fiber and the internal reflecting surface small.

The light source for example comprises a laser. The reflector is preferably axisymmetric so that it provides a light ring around the axis. The light ring may be a complete ring, but it may instead comprise a discontinuous ring of illuminated portions. The cap may have a radial light output window arrangement so that light can only escape through the output window.

The reflecting surface of the cap may be curved. The curvature can be chosen such that the reflected light is collimated. In this way, the single reflector part functions both to redirect and to collimate the light. The reflecting face of the ferrule may be conical so that it maintains the collimation provided the reflecting surface of the cap. Instead, the two reflecting surfaces may together provide the collimation function. The cap and the ferrule may comprise separate parts which are mounted during assembly, or they may form a single integrated component.

In another set of examples, instead of using a reflector cap and a reflecting face of the ferrule, a reflector is mounted inside a central bore of the ferrule that extends beyond the end of the fiber. This central bore thus receives the fiber end as well as the reflector.

This design enables a small outer radius because the reflector is mounted within the ferrule.

In one implementation, the reflector has a reflecting outer face which faces the end of the optical fiber, and the ferrule is transparent. The reflecting outer face directs light outwardly so that it can pass through the surrounding transparent ferrule. In this case, light reflects off the reflecting outer face without entering the body of the reflector.

In another implementation, the reflector has a reflecting inner face, the reflector piece is transparent, and the reflecting inner face is adapted to provide reflection by total internal reflection. In this case, light first enters the body of the reflector (though a surface which faces the end of the optical fiber) and is reflected internally at the reflecting inner face (by total internal reflection), and it then exits the body of the reflector with the desired radial direction.

The reflecting inner face of the reflector may project beyond the end of the ferrule. The ferrule may then be opaque (which gives more options for the choice of material) and only the reflector needs to be formed as a high quality optically transparent piece.

Another aspect of the invention provides a radial illumination system for projecting a light pattern radially comprising:

a light source for generating a light output;

an optical fiber which is adapted to transmit the light output and to emit the light in a direction centered along an axis, from an end of the optical fiber;

a ferrule around the end of the optical fiber; and a reflector coupled to the ferrule, for redirecting the emitted light to form a ring of generally radial light around the axis, wherein the reflector is mounted inside a central bore of the ferrule that extends beyond the end of the fiber, wherein the reflector has a reflecting inner face, the reflector is transparent, and the reflecting inner face is adapted to provide reflection by total internal reflection.

The invention also provides a radial imaging system for capturing an image of an object which extends around an image sensor in an object plane, the system comprising:

a radial illumination system as defined above; and an image sensor for receiving the generally radial light after reflection by the object.

A reflector may be provided for reflecting generally radial light, after reflection by the object, towards the image sensor.

The invention also provides a catheter for use in determining the presence and location of obstructions in an upper airway, the catheter comprising:

at least one radial imaging system as defined above, wherein the image sensor is aligned along or parallel to the catheter axis.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a radial illumination system for projecting a light pattern radially around an axis. A light source generates a light output to an optical fiber. A ferrule is provided around the end of the optical fiber, and a reflector is mounted over or in the ferrule or integral with the ferrule, for redirecting the light to form generally radial light. In this way, a simple design with low component count is able to perform the optical alignment and optical reflecting functions. It may also perform an optical collimation function.

The invention may for example be used for imaging with a conduit. This may have non-medical applications for imaging non-living objects such as pipes, channels and tunnels as well as for medical imaging applications such as for imaging airway passages, intestinal passageway or capillaries or arteries. The imaging system may for example be integrated into a catheter.

Figure 1:
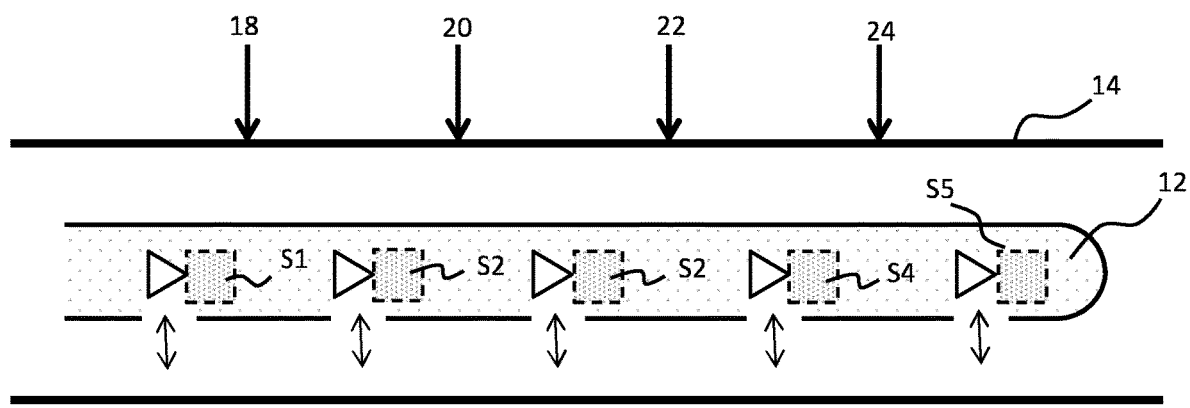
FIG. 1 shows a schematic illustration of a length section of an example catheter disposed inside an airway.

By way of illustration, FIG. 1 schematically depicts an example catheter 12 of known basic configuration, arranged within a stretch of an upper airway 14. Along the length of the airway are indicated four anatomical regions or features, labeled 18, 20, 22, and 24, these, by way of non-limiting example, representing the soft palate (velum), the oropharynx, the tongue base and the epiglottis respectively. Disposed within the airway 14 is the catheter 12, which comprises a series of optical sensors S1 to S5. They each comprise a laser light source for generating light generally axially, a first reflector for redirecting the light to include at least a component in the radial direction, a second reflector for redirecting reflected light from the side wall of the duct being investigated towards an image sensor for capturing an image of side wall of the duct being investigated. From the side wall image, the radial distance to the duct 14 can be determined.

The optical arrangement is represented schematically in FIG. 1 as a single triangle.

Figure 2:
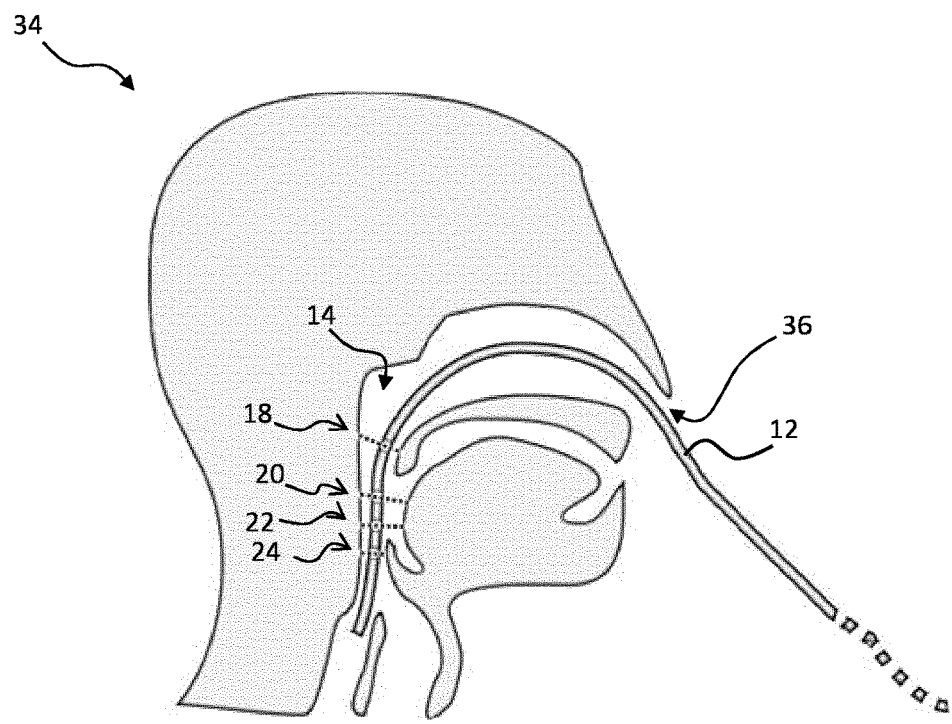
FIG. 2 shows a schematic illustration of an example catheter inserted into a patient's nasal cavity and upper airway.

For illustration, FIG. 2 schematically shows the catheter 12 disposed in the upper airway of a patient 34, having been inserted via the nose 36 of the patient. The approximate positions of the four anatomical regions of FIG. 1 (velum 18, oropharynx 20, tongue base 22, and epiglottis 24) are indicated along the airway 14 of the patient 34.

This invention relates in particular to the arrangement for generating a radial ring of light emitted radially outwardly from the catheter to illuminate a ring shaped section of the wall of the passageway in which the catheter is to be used, e.g. the upper airway 14. The ring may be continuous, but it may instead be formed as a set of discrete points generally following an annular path.

The radial projection may be entirely radial, i.e. at 90 degrees to the catheter axis, but it may be inclined at an acute angle to this perfectly radial direction.

For compactness, for example to fit the optical system within a catheter, the light is routed axially along the catheter, and a reflection arrangement redirects the light to form the radial pattern.

Figure 3A:
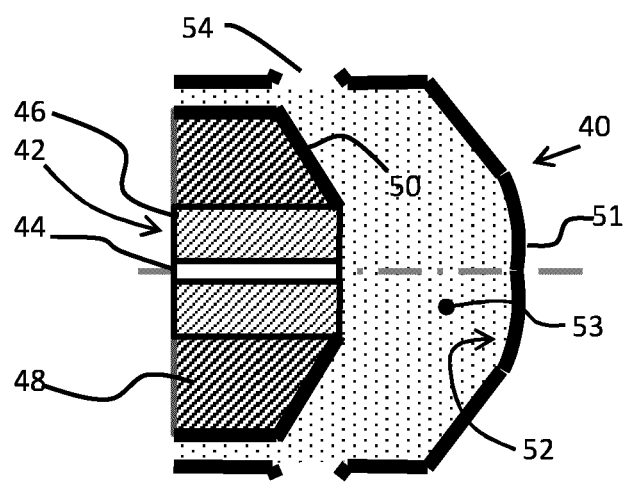
FIG. 3A shows a first example of radial illumination system.
Figure 3B:
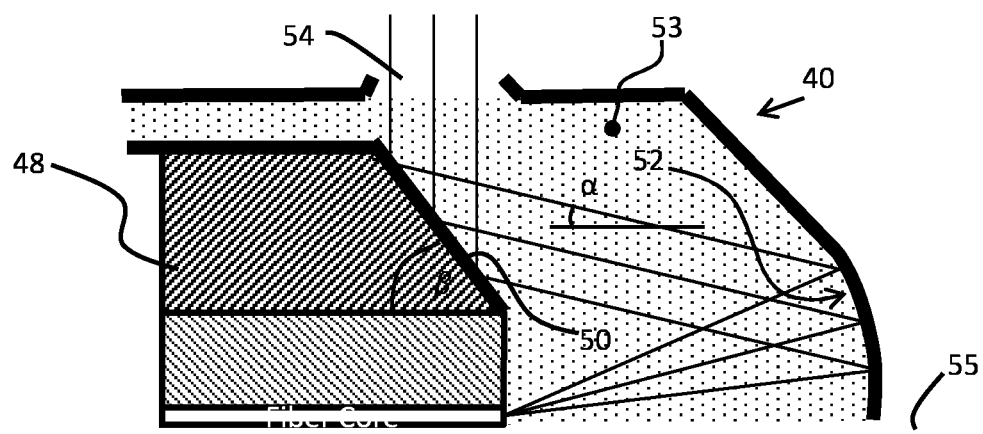
FIG. 3B shows the example of FIG. 3A with typical light rays added to illustrate the reflection and collimation.

FIGS. 3A and 3B show a first example of optical design in accordance with the invention, which is for converting axial light into the radial ring of light.

FIG. 3A shows a cap assembly 40 for mounting over the end of a cleaved optical fiber 42. The optical fiber 42 has a fiber core 44 and a surrounding fiber cladding 46, and it delivers laser light from a laser source. The fiber has an outer buffer further back from the cap assembly, but this is stripped back to fit the cap assembly.

The purpose of the cap assembly 40 is to provide optical coupling to the optical fiber and also to provide redirection of the laser light to a more radial direction, i.e. to a direction which includes a radial component. The cap assembly 40 comprises a ferrule 48 which sits over the end of the fiber. An outer surface 50 of the forward facing end of the ferrule 48 is reflective, either because the ferrule is made from a reflective material or because it is coated with a reflective coating.

The cap assembly 40 further comprises an outer cap 51. This comprises a solid transparent part 53 which fits over the ferrule. It has a reflecting surface 52 which faces the cleaved end of the optical fiber 42 and thereby reflects light which has passed to the surface 52 from the optical fiber. Thus, the outer surface of the cap 51 defines a reflecting surface which faces the interior volume defined by the cap. The purpose of this reflecting surface 52 is to reflect the light which has been emitted from the end of the optical fiber, so that it is redirected towards the reflective outer surface 50. The outer surface 50 then reflects that light to the desired radial or partially radial direction. The light then escapes through an exit window 54.

The ferrule 48 is designed so that the fiber end fits very accurately in a center bore within the ferrule 48. The material of the ferrule 48 in this example does not have to be transparent. The ferrule has an axisymmetric layout so that it directs light in a ring (which may be discontinuous) around the catheter.

As mentioned above, at the fiber end, the outer buffer is stripped from the core and cladding to reveal the fiber end which then fits in the ferrule. The outer surface of the ferrule 48 is also very accurate and is used to center the position of the outer cap 51.

The outer cap 51 is made of a transparent (optical quality) material with reflective coatings such that there is reflection at the internal surfaces other than at the light exit window 54. The light exit window is then a complete ring. For the reflecting outer surface 50, the reflection may be provided by a coating over the ferrule or else the material of the ferrule 48 may provide the required reflection.

The outside of the cap 51 may be coated completely to provide the reflecting surface 52, provided the annular window 54 is either excluded or is processed afterwards. To avoid parasitic reflections, an optical glue can be used to bond the ferrule 48 and the cap 51.

FIG. 3B shows the optical paths through the cap assembly 40. The dimensions are chosen to facilitate the explanation, and only the top part half is shown.

The beam from the fiber core is slightly divergent, and the two reflections (from surface 52 and then surface 50) mentioned above are shown. The internal reflecting surface 52 for example has an essentially parabolic shape, and it projects the rays back with a slight angle α with respect to the axial direction 55. The surface shape is such that this angle α is equal for all rays, so the reflective surface 52 reflects and collimates at the same time.

The reflective outer surface 50 forms a frustum ring that in a preferred example makes an angle of β=45+α/2 degrees with respect to the axial direction. In this way, it redirects the rays in a purely radial direction. Light can freely pass in a radial direction through the exit window 54.

As shown in FIGS. 3A and 3B, the outer cap 51 and the ferrule 48 may be separate parts which are mounted together for instance using transparent glue with refractive index matching the components.

Figure 4:
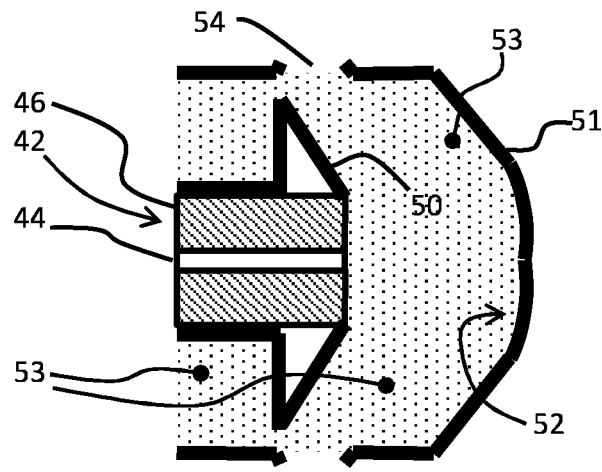
FIG. 4 shows a second example of radial illumination system.

Alternatively, as shown in FIG. 4, the cap part may be integrated with the ferrule into a single integrated capped ferrule in the form of a single solid body 53. It needs to have reflective surfaces to define the surfaces 50 and 52 and it needs a transmissive opening at least at the end of the optical fiber and at the optical window 54. Again, this can be achieved using a patterned reflecting outer coating over the material of the body 53.

The two examples above make use of a cap 51 which fits around or is integrated with the ferrule.

Figure 5:
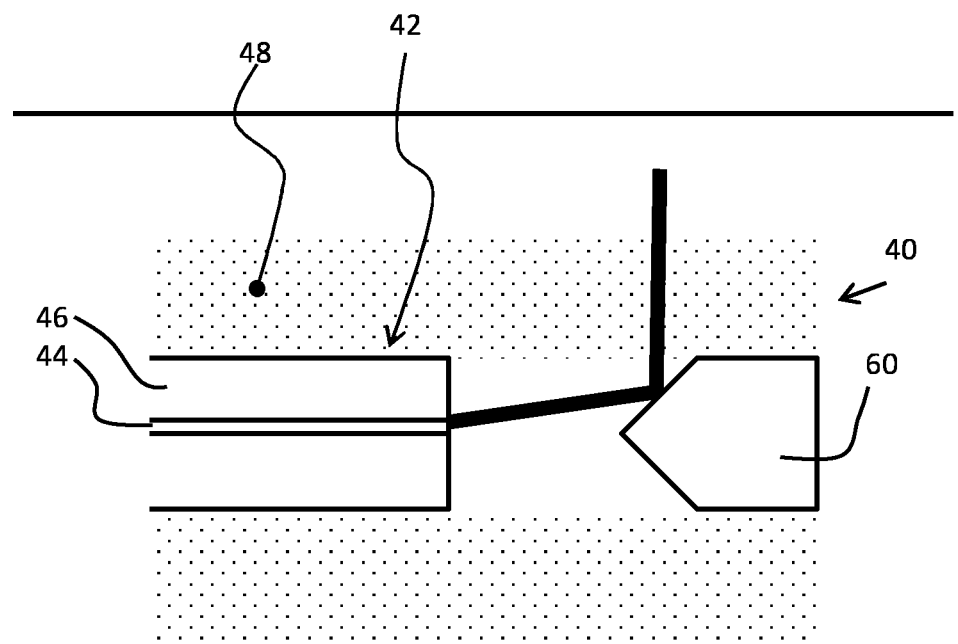
FIG. 5 shows a third example of radial illumination system.

FIG. 5 shows an alternative in which there is a reflector within a ferrule.

The cap assembly 40 comprises a ferrule 48 which again sits around the fiber cladding 46, but it extends beyond the cleaved end of the fiber 42. In this way, the inner bore of the ferrule 48 defines a passageway which extends beyond the end of the fiber 42.

A reflector piece 60 is inserted in this passageway so that it is positioned in front of the fiber end. It terminates the structure in the example shown. It redirects the axial light (i.e. light which is centered on the axial direction but which has a degree of divergence as explained above) to the desired radial direction.

The ferrule is long enough to fit accurately around the fiber at one end but also to have room for the reflector piece 60 inserted at the other end.

In FIG. 5, the reflector piece 60 is a reflective solid body and the ferrule 48 is transparent. The reflector piece 60 has a reflecting outer surface, which defines an essentially conical surface. The light path from the optical fiber is directly to this conical surface, which is shaped so that the received light from the cleaved end of the optical fiber is redirected to the desired radial direction. The light does not enter the body of the reflector piece 60. The reflecting surface may have a planar conical surface or a curved reflecting surface in order to convert the angular light distribution from the fiber core to a collimated radial beam. The radial light passes through the transparent ferrule 48.

Figure 6:
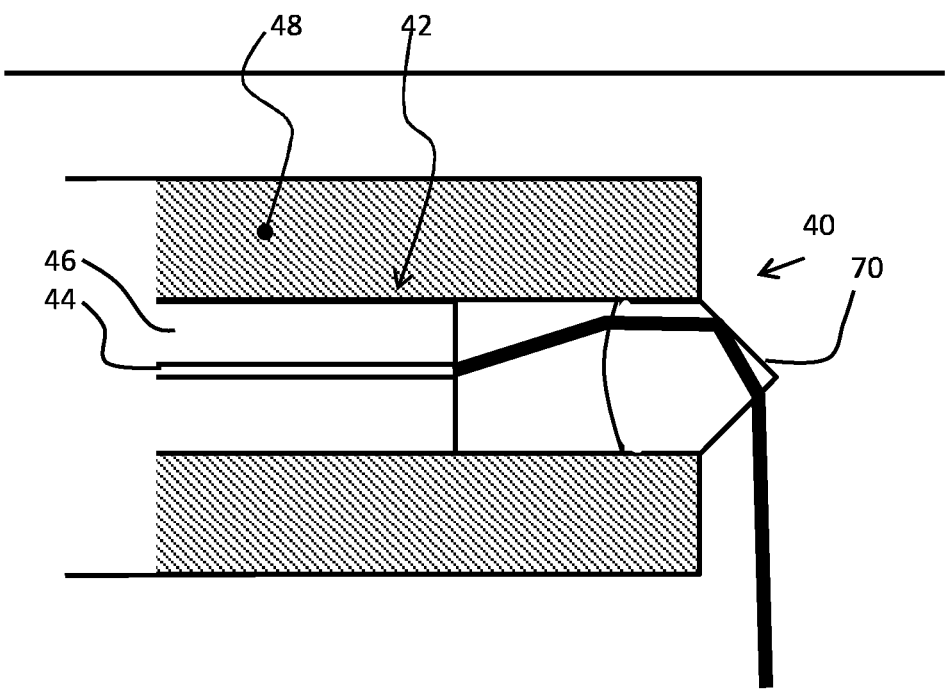
FIG. 6 shows a fourth example of radial illumination system.

FIG. 6 shows a variation in which the reflector piece 70 has its reflecting surface at the other side. Light enters the reflector piece 70 at an entrance surface facing the fiber end and is then reflected by total internal reflection and also refracted, in order to result in the desired radial light output direction.

The total internal reflection surface of the reflector piece 70 is essentially conical, and it projects beyond the end of the ferrule so that a radial light escape path is formed past the end of the ferrule as shown. The ferrule is then non-transparent whereas the reflector piece 70 is fully transparent. The entrance side of the reflector piece (facing the optical fiber) may have a lensing surface (as schematically shown) to provide collimation.

These designs make use of a common fiber optic ferrule both for accurate alignment of the fiber end and for radial light redirection.

The ferrule may be made using standard materials and manufacturing techniques. By way of example, the material of the ferrule may be:

ARCAP AP 1D: this is a non-ferrous copper-nickel-zinc alloy, meeting the requirements of automatic lathe performance and proving an ease of machinability.

Nickel Silver NM2 (CuNi7Zn39Mn2Pb3);

Stainless Steel, for example grade 303;

Borosilicate glass.

The radial output of the device forms a laser plane

Figure 7:
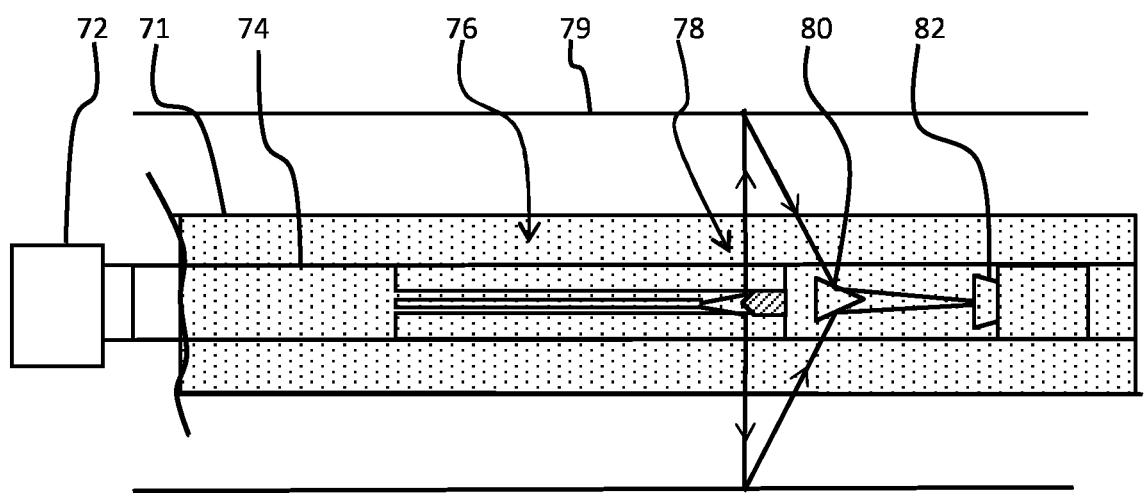
FIG. 7 shows the use of the radial illumination system in a catheter.

FIG. 7 shows an illustrative example of a catheter 71 incorporating a radial illumination system as described above. The catheter 71 is encapsulated within a transparent capillary, and comprises a laser 72, arranged to propagate generated laser light in an axial direction along the optical fiber 74. The laser is mounted at the end of the optical fiber. The optical fiber has an end portion 76 with an outer buffer stripped back so that the core and cladding are retained in the ferrule of the radial illumination system 78.

The radial illumination system generates the radial light output, and after reflection by the channel in which the catheter is mounted (for example a patient airway 79), it is reflected by a cone reflector 80 towards an image sensor 82.

The radial illumination system can be used in any application that uses forward looking light source and where a radial illumination ring is needed.

The reflector used in the example given is axisymmetric, i.e. rotationally symmetric about the central axis along which the fiber runs. However, it may not extend completely around the axis. For example, it may be desired to image to one side only of a plane, in which case a half cone is needed. Thus, an imaging system may be for capturing an image of an object which extends only partially and not fully around an image sensor in the object plane. Similarly, the reflector may be formed of discontinuous circumferential sections if a continuous ring image is not needed.

The invention combines a reflector and a ferrule around the end of the optical fiber. In one example above, a reflecting cap redirects light back to the ferrule (which terminates at the end of the fiber) for a second reflection. In another example, a single reflector is mounted in a ferrule which extends beyond the end of the fiber. There are other possibilities. For example, a cap may be provided over an extended ferrule, with the cap providing the single reflection of light which then passes through the extended end part of the ferrule. Thus, a reflecting cap, an internal reflector within the ferrule, and a reflector formed as part of the ferrule itself, may be combined in various different ways.

One application of particular interest is to improve the performance of an optical catheter sensor for measuring the upper airway patency in OSA patients during natural (or sedated) sleep; in this application a laser plane is created in the sensor module that is perpendicular to the image sensor and cone axis and in the associated cross section in the upper airway a contour lights up. The sensor elements are contained in a capillary.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A radial illumination system for projecting a light pattern radially comprising:
   a light source for generating a light output;
   an optical fiber which is adapted to transmit the light output and to emit the light in a direction centered along a longitudinal axis of the optical fiber, from an end of the optical fiber;
   a ferrule coupled to the end of the optical fiber such that the end of the optical fiber is enveloped within the ferrule; and
   a reflector coupled to or integral with the ferrule, for redirecting the emitted light in a direction disposed perpendicular to the longitudinal axis to form a ring of generally radial light around the axis such that the radial light is directed in and illuminates in the direction disposed perpendicular to the longitudinal axis,
   wherein the ferrule comprises a reflecting face which faces away from the end of the optical fiber, and the reflector comprises a cap which is mounted over an end of the ferrule and which has a reflecting surface which faces the end of the optical fiber, such that an optical path is defined from the end of the optical fiber, to the reflecting surface and then to the reflecting face,
   wherein the optical fiber is coaxial with the light output, and
   wherein the optical fiber is disposed between the light output and the reflector such that the light output must travel through the optical fiber in order to reach the reflector.

2. The radial illumination system of claim 1, wherein the light source comprises a laser.

3. The radial illumination system of claim 1, wherein the reflector is axisymmetric.

4. The radial illumination system of claim 1, wherein the cap has a radial light output window arrangement.

5. The radial illumination system of claim 1, wherein the reflecting surface of the cap is curved, such that the reflected light is collimated.

6. The radial illumination system of claim 1, wherein the reflecting face of the ferrule is conical.

7. The radial illumination system of claim 1, wherein the cap and the ferrule comprise a single integrated component.

8. A radial imaging system for capturing an image of an object which extends around an image sensor in an object plane, the system comprising:
   the radial illumination system of claim 1; and
   an image sensor for receiving the generally radial light after reflection by the object.

9. The radial imaging system of claim 8, comprising a reflector for reflecting generally radial light after reflection by the object towards the image sensor.

10. A catheter for use in determining the presence and location of obstructions in an upper airway, the catheter comprising:
    at least one of the radial imaging system of claim 8, wherein the image sensor is aligned along or parallel to the catheter axis.

11. A radial illumination system for projecting a light pattern radially comprising:
    a light source for generating a light output;
    an optical fiber which is adapted to transmit the light output and to emit the light in a direction centered along a longitudinal axis of the optical fiber, from an end of the optical fiber;
    a ferrule coupled to the end of the optical fiber such that the end of the optical fiber is enveloped within the ferrule; and
    a reflector coupled to the ferrule, for redirecting the emitted light in a direction disposed perpendicular to the longitudinal axis to form a ring of generally radial light around the axis such that the radial light is directed in and illuminates in the direction disposed perpendicular to the longitudinal axis, wherein the reflector is mounted inside a central bore of the ferrule that extends beyond the end of the fiber, wherein the reflector has a reflecting inner face, the reflector is transparent, and the reflecting inner face is adapted to provide reflection by total internal reflection,
    wherein the optical fiber is coaxial with the light output, and
    wherein the optical fiber is disposed between the light output and the reflector such that the light output must travel through the optical fiber in order to reach the reflector.

12. The radial illumination system of claim 11, wherein the reflecting inner face of the reflector projects beyond the end of the ferrule.

13. The radial illumination system of claim 11, wherein the light source comprises a laser.

14. The radial illumination system of claim 11, wherein the reflector is axisymmetric.

* * * * *